US012329651B2

(12) United States Patent
Bray, Jr.

(10) Patent No.: US 12,329,651 B2
(45) Date of Patent: Jun. 17, 2025

(54) ARTIFICIAL DISC REPLACEMENT DEVICE

(71) Applicant: Robert S. Bray, Jr., Newport Beach, CA (US)

(72) Inventor: Robert S. Bray, Jr., Newport Beach, CA (US)

(73) Assignee: TRM IP Management, LLC, Newport Beach, CA (US)

(*) Notice: Subject to any disclaimer, the term of this patent is extended or adjusted under 35 U.S.C. 154(b) by 0 days.

(21) Appl. No.: 18/615,354

(22) Filed: Mar. 25, 2024

(65) Prior Publication Data
US 2024/0225852 A1 Jul. 11, 2024

Related U.S. Application Data

(63) Continuation of application No. 17/526,047, filed on Nov. 15, 2021, now Pat. No. 11,938,035, which is a continuation of application No. 16/702,686, filed on Dec. 4, 2019, now Pat. No. 11,197,765.

(51) Int. Cl.
A61F 2/44 (2006.01)
A61F 2/30 (2006.01)

(52) U.S. Cl.
CPC .. *A61F 2/4425* (2013.01); *A61F 2002/30014* (2013.01); *A61F 2002/443* (2013.01); *A61F 2002/448* (2013.01)

(58) Field of Classification Search
CPC .......... A61F 2002/30014; A61F 2/4425; A61F 2002/443
See application file for complete search history.

(56) References Cited

U.S. PATENT DOCUMENTS

| 5,401,269 A | 3/1995 | Buttner-Janz et al. |
| 5,888,226 A * | 3/1999 | Rogozinski ........... A61F 2/4425 623/17.16 |
| 6,402,785 B1 | 6/2002 | Zdeblick et al. |
| 6,648,917 B2 | 11/2003 | Gerbec |
| 6,682,562 B2 | 1/2004 | Viart et al. |

(Continued)

FOREIGN PATENT DOCUMENTS

| DE | 20310432 | 10/2003 |
| IT | BO20100597 | 4/2012 |

(Continued)

OTHER PUBLICATIONS

Office Action mailed Mar. 2, 2021 in U.S. Appl. No. 16/702,686.

(Continued)

*Primary Examiner* — Larry E Waggle, Jr.
(74) *Attorney, Agent, or Firm* — Plumsea Law Group, LLC

(57) ABSTRACT

An artificial disc replacement device is disclosed. The device includes an upper endplate and a lower endplate, as well as a core assembly disposed between the endplates. The core assembly includes a core member with a curved engaging surface and a matrix member. The matrix member is more compressible than the core member. The curved engaging surface of the core member engages a recess in the upper endplate so that the upper endplate can translate along the curved engaging surface. The curved engaging surface has a greater curvature at its posterior end than at its anterior end to facilitate different ranges of motion during extension and flexion.

14 Claims, 13 Drawing Sheets

(56) References Cited

U.S. PATENT DOCUMENTS

| | | |
|---|---|---|
| 6,964,686 B2 | 11/2005 | Gordon |
| 7,011,684 B2 | 3/2006 | Eckman |
| 7,022,139 B2 | 4/2006 | Errico et al. |
| 7,118,599 B2 | 10/2006 | Errico et al. |
| 7,160,327 B2 | 1/2007 | Errico et al. |
| 7,217,291 B2 | 5/2007 | Zucherman et al. |
| 7,223,291 B2 | 5/2007 | Errico et al. |
| 7,267,688 B2 | 9/2007 | Ferree |
| 7,326,250 B2 | 2/2008 | Beaurain et al. |
| 7,331,994 B2 | 2/2008 | Gordon et al. |
| RE40,260 E | 4/2008 | Buhler |
| 7,442,211 B2 | 10/2008 | de Villiers et al. |
| 7,481,840 B2 | 1/2009 | Zucherman et al. |
| 7,491,241 B2 | 2/2009 | Errico et al. |
| 7,517,363 B2 | 4/2009 | Rogers et al. |
| 7,563,284 B2 | 7/2009 | Coppes et al. |
| 7,563,286 B2 | 7/2009 | Gerber et al. |
| 7,621,956 B2 | 11/2009 | Paul et al. |
| 7,641,666 B2 | 1/2010 | Paul et al. |
| 7,690,381 B2 | 4/2010 | Bartish, Jr. et al. |
| 7,695,516 B2 | 4/2010 | Zeegers |
| 7,708,777 B2 | 5/2010 | O'Neil et al. |
| 7,731,753 B2 | 6/2010 | Reo et al. |
| 7,771,479 B2 | 8/2010 | Humphreys et al. |
| 7,811,326 B2 | 10/2010 | Braddock, Jr. et al. |
| 7,842,089 B2 | 11/2010 | Aaron |
| 7,909,877 B2 | 3/2011 | Krueger et al. |
| 7,927,374 B2 | 4/2011 | Duggal et al. |
| 7,951,200 B2 | 5/2011 | Heinz |
| 7,963,994 B2 | 6/2011 | Biedermann et al. |
| 8,002,835 B2 | 8/2011 | Zeegers |
| 8,038,713 B2 | 10/2011 | Ferree |
| 8,038,716 B2 | 10/2011 | Duggal et al. |
| 8,100,974 B2 | 1/2012 | Duggal et al. |
| 8,118,873 B2 | 2/2012 | Humphreys et al. |
| 8,142,505 B2 | 3/2012 | Tauber |
| 8,152,850 B2 | 4/2012 | Copf, Jr. |
| 8,163,023 B2 | 4/2012 | Nguyen et al. |
| 8,172,902 B2 | 5/2012 | Kapitan et al. |
| 8,241,360 B2 | 8/2012 | Bao et al. |
| 8,366,775 B2 | 2/2013 | Errico et al. |
| 8,382,843 B2 | 2/2013 | Laurence et al. |
| 8,425,606 B2 | 4/2013 | Cowan |
| 8,496,713 B2 | 7/2013 | Bennett et al. |
| 8,535,379 B2 | 9/2013 | Moskowitz et al. |
| 8,545,564 B2 | 10/2013 | Errico et al. |
| 8,613,771 B2 | 12/2013 | Hansell et al. |
| 8,679,181 B2 | 3/2014 | Lechmann et al. |
| 8,728,163 B2 | 5/2014 | Theofilos et al. |
| 8,747,471 B2 | 6/2014 | Albans et al. |
| 8,882,842 B2 | 11/2014 | Bergagnoli |
| 8,998,990 B2 | 4/2015 | Bertagnoli et al. |
| 9,005,290 B2 | 4/2015 | Morrison, III |
| 9,011,493 B2 | 4/2015 | Zappacosta et al. |
| 9,011,544 B2 | 4/2015 | Arramon et al. |
| 9,017,410 B2 | 4/2015 | Hansell et al. |
| 9,066,809 B2 | 6/2015 | Hansell et al. |
| 9,101,485 B2 | 8/2015 | Berger et al. |
| 9,125,753 B2 | 9/2015 | Caballes |
| 9,138,329 B2 | 9/2015 | McCombe et al. |
| 9,198,697 B2 | 12/2015 | Zappacosta |
| 9,198,770 B2 * | 12/2015 | Balasubramanian ... A61F 2/442 |
| 9,237,958 B2 | 1/2016 | Duggal et al. |
| 9,308,101 B2 | 4/2016 | Doty |
| 9,468,537 B2 | 10/2016 | Cowan |
| 9,486,251 B2 | 11/2016 | Zappacosta et al. |
| 9,642,718 B2 | 5/2017 | Sournac et al. |
| 10,039,575 B2 | 8/2018 | Fortin et al. |
| 10,307,263 B2 | 6/2019 | Dzioba |
| 10,376,385 B2 | 8/2019 | Gray et al. |
| 11,197,765 B2 * | 12/2021 | Bray, Jr. ............ A61F 2/4425 |
| 11,839,554 B2 | 12/2023 | Bray, Jr. |
| 2003/0233097 A1 | 12/2003 | Ferree |
| 2003/0233148 A1 | 12/2003 | Ferree |
| 2004/0030390 A1 | 2/2004 | Ferree |
| 2004/0044410 A1 | 3/2004 | Ferree |
| 2004/0059318 A1 | 3/2004 | Zhang |
| 2004/0127991 A1 | 7/2004 | Ferree |
| 2004/0148027 A1 | 7/2004 | Errico |
| 2004/0186577 A1 | 9/2004 | Ferree |
| 2005/0027364 A1 | 2/2005 | Kim |
| 2005/0038515 A1 | 2/2005 | Kunzler |
| 2005/0085911 A1 | 4/2005 | Link |
| 2005/0149189 A1 | 7/2005 | Mokhtar et al. |
| 2005/0165407 A1 | 7/2005 | Diaz |
| 2005/0171610 A1 | 8/2005 | Humphreys et al. |
| 2005/0234553 A1 | 10/2005 | Gordon |
| 2006/0020341 A1 | 1/2006 | Schneid et al. |
| 2006/0069438 A1 | 3/2006 | Zucherman et al. |
| 2006/0069441 A1 | 3/2006 | Zucherman et al. |
| 2006/0089656 A1 | 4/2006 | Allard |
| 2006/0116768 A1 | 6/2006 | Krueger et al. |
| 2006/0136063 A1 | 6/2006 | Zeegers |
| 2006/0149371 A1 | 7/2006 | Marik et al. |
| 2006/0235524 A1 | 10/2006 | Petit et al. |
| 2006/0235528 A1 | 10/2006 | Buettner-Janz |
| 2007/0050030 A1 | 3/2007 | Kim |
| 2007/0050032 A1 | 3/2007 | Gittings et al. |
| 2007/0100456 A1 | 5/2007 | Dooris |
| 2007/0162137 A1 | 7/2007 | Kloss |
| 2007/0168037 A1 | 7/2007 | Posnick |
| 2007/0209222 A1 | 9/2007 | Fischer |
| 2007/0270631 A1 | 11/2007 | Nelson |
| 2008/0015699 A1 | 1/2008 | Voydeville |
| 2008/0065216 A1 | 3/2008 | Hurlbert et al. |
| 2008/0114453 A1 | 5/2008 | Francis |
| 2008/0161924 A1 | 7/2008 | Viker |
| 2008/0183204 A1 | 7/2008 | Greenhalgh |
| 2008/0195206 A1 | 8/2008 | Chee et al. |
| 2008/0215156 A1 | 9/2008 | Duggal |
| 2009/0005872 A1 | 1/2009 | Moumene |
| 2009/0210059 A1 | 8/2009 | McCombe |
| 2010/0082110 A1 | 4/2010 | Belliard |
| 2010/0241231 A1 | 9/2010 | Marino |
| 2010/0292801 A1 | 11/2010 | Hansell |
| 2011/0125270 A1 | 5/2011 | Paul |
| 2011/0202135 A1 | 8/2011 | Baek |
| 2011/0257748 A1 | 10/2011 | Liu |
| 2011/0264223 A1 | 10/2011 | Lemaire et al. |
| 2014/0236297 A1 | 8/2014 | Iott |
| 2015/0018952 A1 | 1/2015 | Ali |
| 2015/0039089 A1 | 2/2015 | Balasubramanian |
| 2015/0196399 A1 | 7/2015 | Hansell et al. |
| 2017/0202676 A1 | 7/2017 | Muhlbrauer |
| 2019/0008651 A1 | 1/2019 | Doty |
| 2019/0231550 A1 | 8/2019 | Dzioba |
| 2019/0254721 A1 | 8/2019 | Zappacosta |
| 2019/0254834 A1 | 8/2019 | Balasubramanian et al. |

FOREIGN PATENT DOCUMENTS

| | | |
|---|---|---|
| WO | WO 03084449 | 10/2003 |
| WO | WO 2004016217 | 2/2004 |
| WO | WO 2005032431 | 4/2005 |
| WO | WO 2006016384 | 2/2006 |
| WO | WO 2008010240 | 1/2008 |
| WO | WO 2009118691 | 10/2009 |
| WO | WO 2018114334 | 6/2018 |

OTHER PUBLICATIONS

Office Action mailed May 19, 2023 in U.S. Appl. No. 17/526,047.
Notice of Allowance mailed Nov. 3, 2023 in U.S. Appl. No. 17/526,047.
International Search Report dated May 25, 2021 in PCT/US2020/062590.
Office Action mailed Feb. 21, 2023 in U.S. Appl. No. 17/156,179.
Extended European Search Report dated Dec. 15, 2023 in European Application No. 20895258.0-1122.
Office Action mailed Sep. 12, 2024 in U.S. Appl. No. 18/533,908.

(56) References Cited

OTHER PUBLICATIONS

Office Action mailed Oct. 29, 2024 in U.S. Appl. No. 18/615,354.

* cited by examiner

ARTIFICIAL DISC REPLACEMENT DEVICE

CROSS-REFERENCE TO RELATED APPLICATIONS

This application is a continuation of U.S. application Ser. No. 17/526,047, filed Nov. 15, 2021, and titled "Artificial Disc Replacement Device," which is a continuation of U.S. application Ser. No. 16/702,686, filed Dec. 4, 2019, and titled "Artificial Disc Replacement Device," now U.S. Pat. No. 11,197,765, issued Dec. 14, 2021. Each of the applications listed above is incorporated herein by reference in its entirety.

BACKGROUND

The embodiments are generally directed to implants for the spine, and in particular to artificial disc replacements.

An artificial disc, also known as artificial disc replacement (ADR), is a medical device implanted into the spine that acts as, or imitates, a spinal disc. Surgeons can replace the entire disc or remove only the nucleus (center of the disc). ADR devices may be designed to allow for motion between the adjacent vertebra, rather than fuse adjacent vertebrae together as occurs in other kinds of spinal implants.

Current ADR systems may impede normal movement in the back and/or neck. For example, some systems allow vertebrae to pivot around a fixed central point but prevent the vertebrae from translating during flexion. Other ADR systems include a mobile core that can slide along one or both endplates. These mobile cores may become displaced from their intended range of motion, or their range of motion may be affected by scarring of the adjacent tissue, which may result in failure of the ADR and/or a limited range of motion. Also, in current ADR systems, the upper and lower endplates may come into contact during flexion and/or extension, thereby requiring the use of high strength materials such as metals. The use of metallic endplates may create unwanted visual artifacts during magnetic resonance imaging (MRI) of the patients spine. These MRI artifacts may make it difficult for a radiologist and/or surgeon to accurately assess the state of the spine or surrounding tissue.

There is a need in the art for a system and method that addresses the shortcomings discussed above.

SUMMARY

In one aspect, an artificial disc replacement device includes a first endplate configured to be disposed against a first vertebrae in a spine and a second endplate configured to be disposed against a second vertebrae in the spine. The device also includes a core assembly comprising a core member and a matrix member, where the core member includes a base portion and a curved engaging surface, and where the base portion of the core member is embedded in the matrix member. The first endplate includes a first recess for receiving the curved engaging portion of the core member and the second endplate includes a second recess for receiving the matrix member.

In another aspect, an artificial disc replacement device includes a first endplate configured to be disposed against a first vertebrae in a spine and a second endplate configured to be disposed against a second vertebrae in the spine. The device also includes a core member disposed between the first endplate and the second endplate, the core member having a curved engaging surface for engaging the first endplate. The core member includes a sagittal plane that separates the core member into a first lateral side and a second lateral side. The core member also includes a coronal plane that separates the core member into an anterior side and a posterior side. The curved engaging surface includes a curved boundary that extends within a first plane that is parallel with the sagittal plane. The curved boundary has a first arc radius along an anterior portion disposed on the anterior side of the core member. The curved boundary has a second arc radius along a posterior portion disposed on the posterior side of the curved boundary, where the second arc radius is substantially different from the first arc radius.

In another aspect, an artificial disc replacement device includes a first endplate configured to be disposed against a first vertebrae in a spine and a second endplate configured to be disposed against a second vertebrae in the spine. The device also includes a core member disposed between the first endplate and the second endplate and a matrix member disposed between the first endplate and the second endplate, where the matrix member is in continuous contact with the second endplate. The first endplate includes a recess and where the core member includes a curved engaging surface in continuous contact with the recess. The first endplate can move along the curved engaging surface. The matrix member is disposed between the core member and the second endplate and prevents contact between the core member and the second endplate. The matrix member is positioned to prevent the first endplate from contacting the second endplate as the first endplate moves along the core member.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

DETAILED DESCRIPTION

The embodiments provide a spinal implant in the form of an artificial disc replacement device, also referred to simply as an ADR device. The ADR device can be implanted between adjacent vertebrae in the spine in order to replace damaged spinal discs. The exemplary ADR device is configured with an upper endplate and a lower endplate that sandwich a core assembly. The core assembly includes a core member that is partially embedded within a matrix member. The core member has a convex upward engaging surface. The upward engaging surface varies in curvature along a sagittal plane to facilitate natural motion between the adjacent vertebrae during flexion and extension. Specifically, the posterior portion of the core member has a smaller arc radius (and correspondingly, a larger curvature) than the anterior portion of the core member. This helps limit compression during extension and increases compression and forward translation of the upper endplate during flexion. The upward engaging surface has an approximately constant curvature along a coronal plane to facilitate symmetric lateral bending in either lateral directions.

The exemplary device also uses a matrix member that is less rigid than the core member, thereby improving cushioning and shock absorption. The matrix member may also extend upward from the lower endplate to engage the upper endplate during flexion and extension, thereby preventing the endplates from contacting one another. As the endplates never contact one another they can be constructed from materials other than metal. For example, the endplates may be constructed of ceramic or carbon materials that provide better biocompatibility with vertebra, improved wear characteristics and different degrees of strength compared to metal materials. Additionally, using ceramic or carbon materials may limit or eliminate MRI artifacts that can be caused by using metallic endplates.

Figure 1:
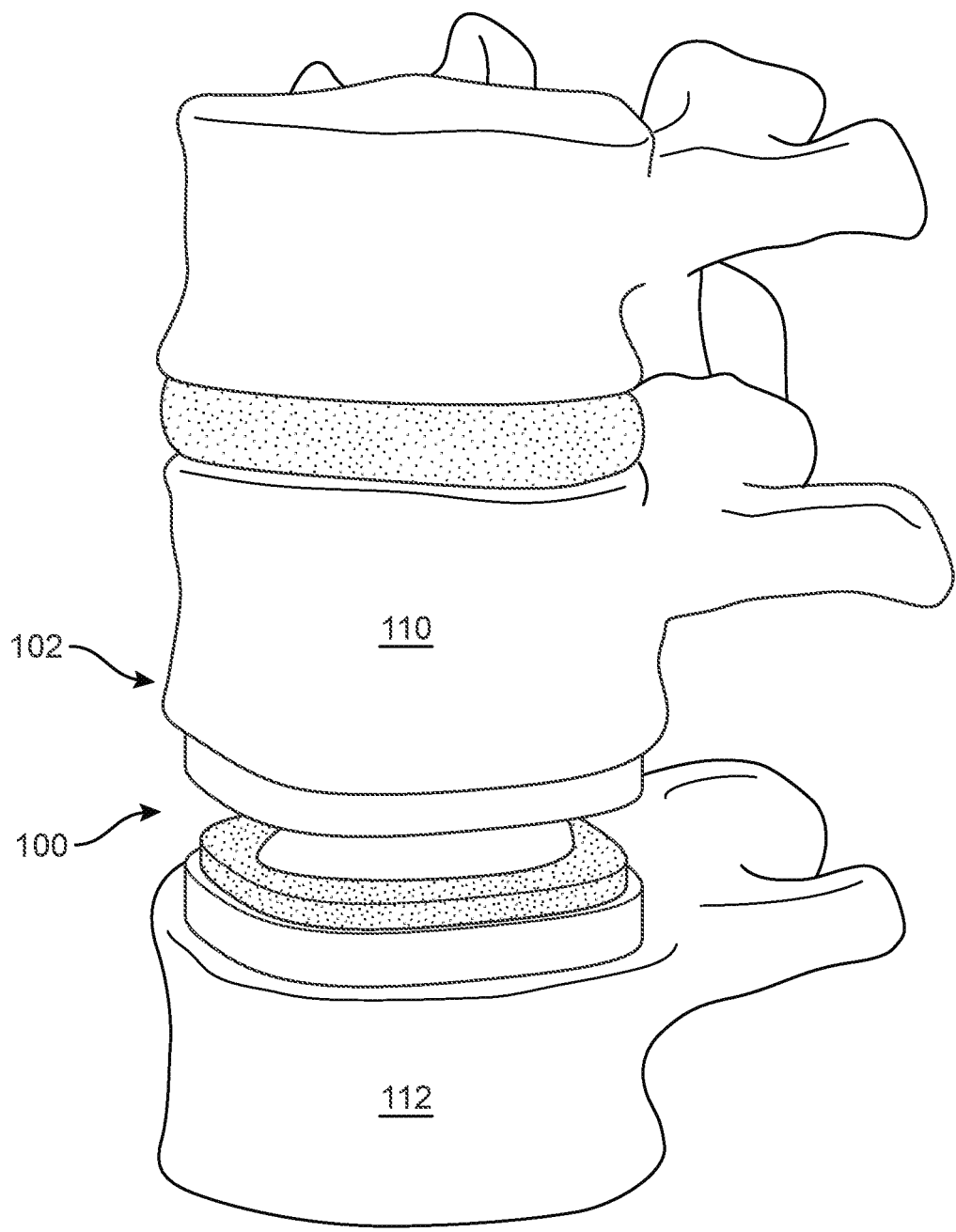
FIG. 1 is a schematic view of a portion of the cervical spine including an artificial disc replacement device disposed between two adjacent cervical vertebrae, according to an embodiment.

FIG. 1 is a schematic view of an embodiment of an implant in the form of an artificial disc replacement device 100, also referred to simply as ADR device 100. In FIG. 1, ADR device 100 is embedded within a portion 102 of a spinal column. Specifically, ADR device 100 is disposed between a first vertebra 110 and a second vertebra 112.

It may be appreciated that the ADR device described in this detailed description and in the claims may be used within any suitable portion of the spine. The embodiment of FIG. 1 depicts ADR device 100 used with lumbar vertebrae. However, other embodiments could include a device that may be used to replace spinal discs in any portion of the spine including the lumbar spine, the thoracic spine, and the cervical spine. For example, the embodiments described below and shown in FIGS. 10-15 depict an ADR device that is implanted between adjacent cervical vertebrae in the neck. It may be appreciated that suitable adjustments could be made to the dimensions and/or geometries of various parts of the ADR device in order to accommodate anatomic differences in the different regions of the spine.

For purposes of clarity, reference is made to various directional adjectives throughout the detailed description and in the claims. As used herein, the term "anterior" refers to a side or portion of an implant that is intended to be oriented towards, or disposed closer to, the front of the human body when the implant has been placed in the body. Likewise, the term "posterior" refers to a side or portion of an implant that is intended to be oriented towards, or disposed closer to, the back of the human body following implantation. Moreover, the posterior side and the anterior side of a body (or part) may be separated by a coronal plane (also known as a frontal plane).

In addition, the term "superior" refers to a side or portion of an implant that is intended to be oriented towards a top (e.g., the head) of the body while "inferior" refers to a side or portion of an implant that is intended to be oriented towards a bottom of the body. Moreover, the superior side and inferior side of the body may be separated by a transverse plane.

Reference is also made herein to "lateral" sides or portions of an implant, which are sides or portions facing along a lateral direction of the body. These lateral sides may be separated by a sagittal plane.

Figure 2:
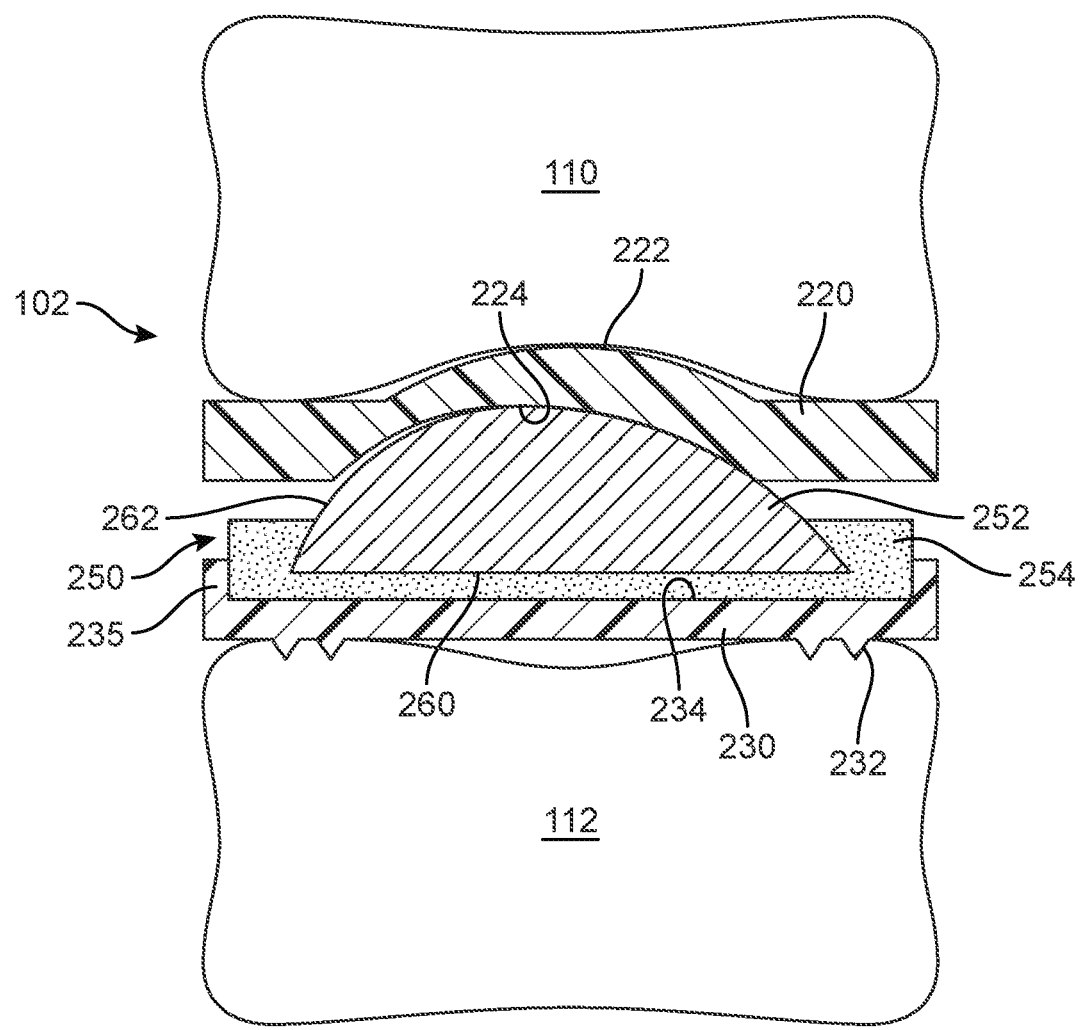
FIG. 2 is a schematic cross-sectional view of the artificial disc replacement device of FIG. 1 including the two adjacent vertebrae.

FIG. 2 is a schematic cross-sectional view of ADR device 100 as it is embedded within portion 102 of the spinal column. ADR device 100 is also shown in isolation in FIG. 3. Additionally, FIG. 4 depicts an exploded isometric view of ADR device 100.

Figure 3:
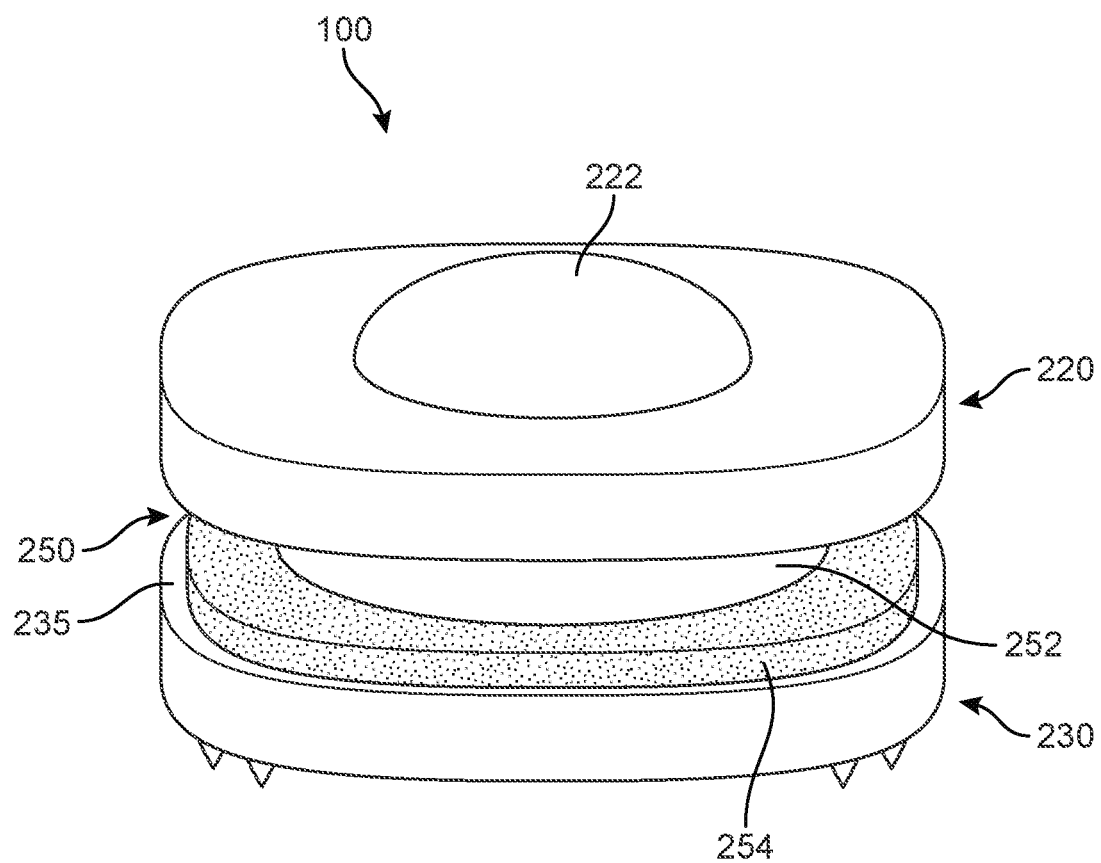
FIG. 3 is a schematic perspective view of the artificial disc replacement device of FIG. 1.
Figure 4:
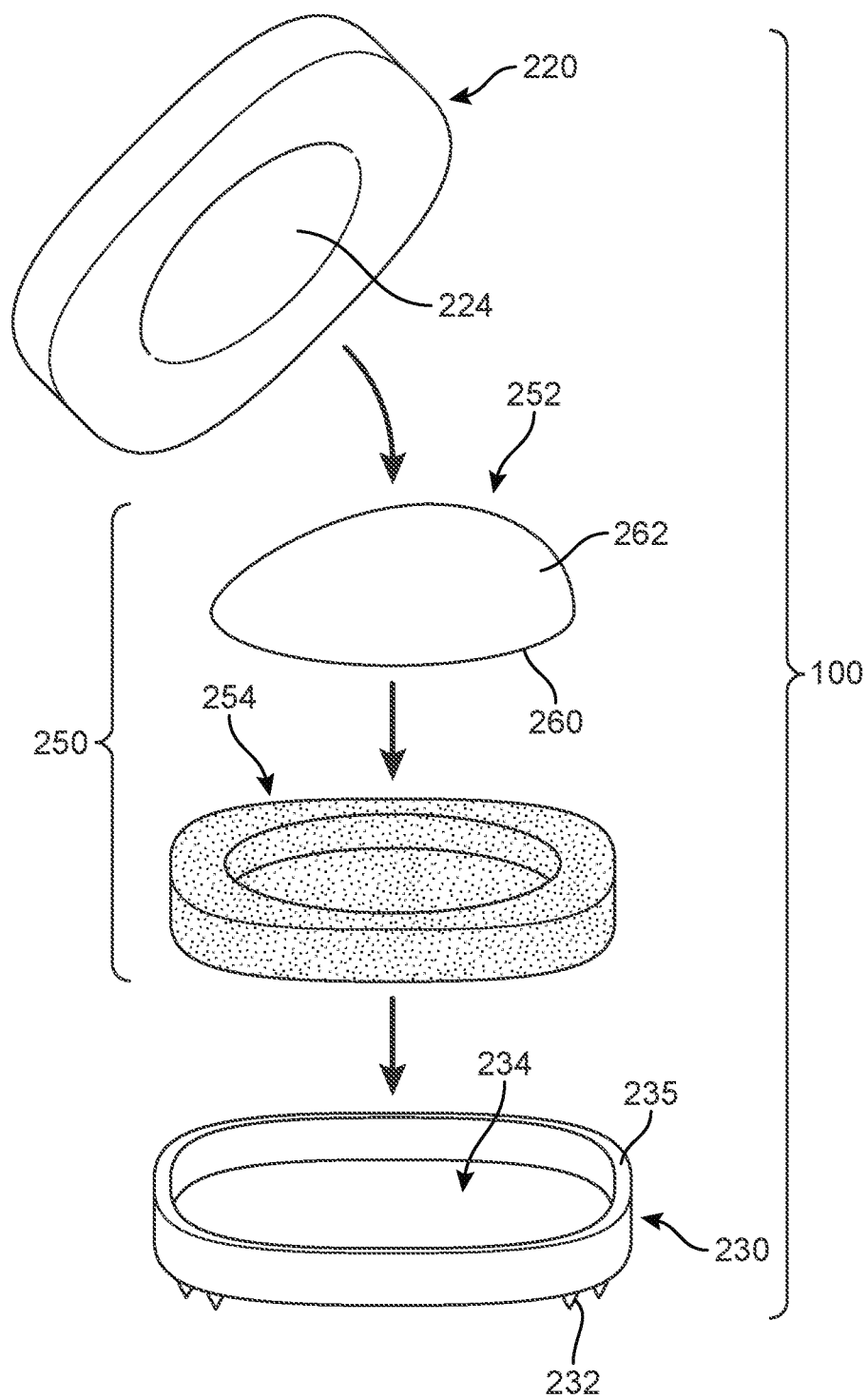
FIG. 4 is a schematic exploded view of the artificial disc replacement device of FIG. 3.

Referring to FIGS. 2-4, ADR device 100 includes a first endplate 220 and a second endplate 230. First endplate 220, which may also be referred to as an upper endplate, is disposed on a superior side of ADR device 100. Second endplate 230, which may also be referred to as a lower endplate, is disposed on an inferior side of ADR device 100.

First endplate 220 may be configured to engage a first vertebra (for example, first vertebra 110 of FIG. 2). In some embodiments, first endplate 220 may include a dome 222 that can be fit into a corresponding recess (or concave area) within first vertebra 110. Dome 222 comprises a protrusion that helps align and hold first endplate 220 in position with respect to first vertebra 110. In particular, dome 222 may help keep first endplate 220 from translating laterally with respect to first vertebra 110.

Second endplate 230 may be configured to engage a second vertebra (for example, second vertebra 112 of FIG. 2). In some embodiments, second endplate 230 may include provisions for permanently attaching to a vertebra. In the exemplary embodiment, second endplate 230 includes a set of teeth 232 that can engage a vertebra.

Although the embodiments depict endplates with domes and/or teeth for engaging vertebrae, in other embodiments any other suitable provisions for attaching endplates to vertebrae could be used. Exemplary mechanisms include, but are not limited to: screws, rods, nails, and blades. In such embodiments, the endplates may be suitably modified to receive at least part of the fastening mechanism. For example, an endplate could include holes for receiving screws.

ADR device 100 may also include a core assembly 250 that is disposed between first endplate 220 and second endplate 230. Core assembly 250 of ADR device 100 may itself comprise two distinct members. Specifically, core assembly 250 comprises a core member 252 and a matrix member 254. Core member 252 further includes a base portion 260 and a curved engaging surface 262. As shown in FIG. 2, base portion 260 of core member 252 may be embedded within matrix member 254.

First endplate 220 may include a recess 224 that receives curved engaging surface 262 of core member 252. As described in further detail below, recess 224 may be sized and shaped to receive different portions of curved engaging surface 262, allowing first endplate 220 to tilt and translate along curved engaging surface 262 so as to facilitate natural motions between adjacent vertebra during flexion, extension, and lateral bending. In the exemplary embodiment shown in FIG. 2, recess 224 extends from an inferior side of first endplate 220 towards a superior side of first endplate 220. However, recess 224 does not extend into the portion of first endplate 220 defined by dome 222. In other embodiments, however, recess 224 could extend into the portion of first endplate 220 defined by dome 222, which may enable the overall thickness of first endplate 220 to be further reduced and/or the depth of recess 224 to be increased.

Second endplate 230 may include a recess 234 that receives matrix member 254. Recess 234 may be bounded by an outer wall or lip 235. In some embodiments, recess 234 is sized and dimensioned to tightly fit matrix member 254 so that, once inserted, matrix member 254 cannot be easily dislodged from recess 234. However, in other embodiments, matrix member 254 can be fixed within recess 234 using a suitable fastener and/or biocompatible adhesive.

Vertebral bodies are comprised of two distinct types of tissue: cortical bone and cancellous bone. The cancellous bone is disposed more centrally within the vertebral body, which is surrounded by an outer layer of cortical bone. At the superior and inferior ends of the vertebral body, the cortical bone forms a raised lip (or cortical rim) around the cancellous bone. Because the rim of cortical bone is denser and generally stronger than the interior cancellous bone, the endplates of the present embodiments are shaped to increase engagement with the cortical rim. Specifically, first endplate 220 and second endplate 230 both have approximately rectangular shapes with rounded corners. This geometry helps ensure that the endplates are supported, at least in part, by the cortical rim of each vertebral body.

Although the embodiments depict endplates with an approximately rectangular geometry, in other embodiments the outer perimeter of each endplate may be varied to approximately match the geometry of the cortical rim of the associated vertebral body. Thus, in some cases, endplates could have a curved front edge that matches the approximate geometry of the anterior lip of the associated vertebral body. Likewise, in some cases, endplates could have lateral and/or posterior edges that match the approximate geometries of the lateral and/or posterior portions of the cortical rim.

Figure 5:
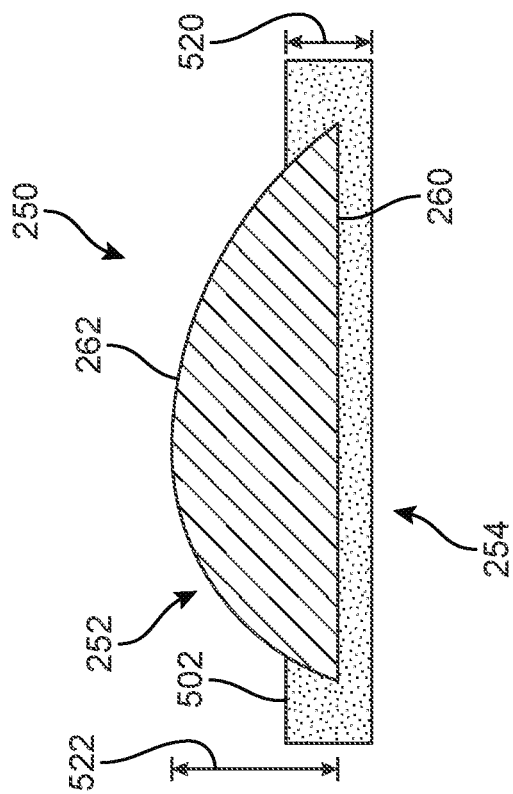
FIG. 5 is a schematic front view of a core assembly including a core member and a matrix member, according to an embodiment.

FIG. 5 is a schematic view of core assembly 250 shown in isolation. As seen in FIG. 5, base portion 260 may be embedded in matrix member 254. That is, base portion 260 may be surrounded from an inferior (lower) side, as well as from the lateral sides, by portions of matrix member 254. However, matrix member 254 does not cover or encase a substantial portion of curved engaging surface 262, which extends out from a superior surface 502 of matrix member 254. With this configuration, curved engaging surface 262 directly engages first endplate 220 (see FIG. 2), while preventing any portion of core member 252 from coming into direct contact with second endplate 230.

Figure 6:
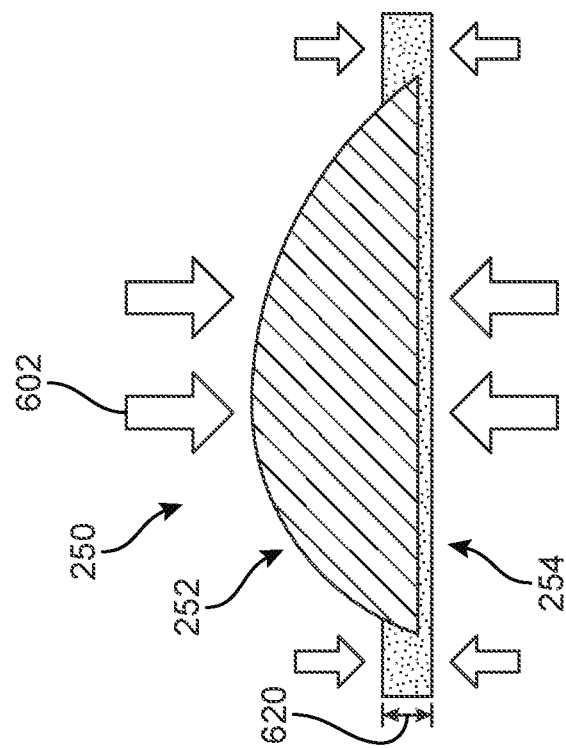
FIG. 6 is a schematic front view of the core assembly of FIG. 5, in which the matrix member deforms under compressive forces.

Core member 252 and matrix member 254 may be made of substantially different materials. In some embodiments, core member 252 may be made of a more rigid material than matrix member 254. Also, matrix member 254 may be made of a substantially more compressible material than core member 252. For example, as seen in FIG. 6, matrix member 254 may undergo substantial compression in a vertical direction under vertical loads 602. By contrast, core member 252 may not compress substantially under these same loads. As seen by comparing FIGS. 5 and 6, the vertical thickness of matrix member 254 may compress from a first thickness 520 to a second thickness 620 while core member 252 maintains a substantially constant thickness 522 before and during compression.

Embedding part of core member 252 within a more flexible and/or compressible matrix material allows for cushioning and shock absorption within ADR device 100. Furthermore, this configuration allows core member 252 to "float" within matrix member 254, thereby providing some relative movement between core member 252 and second endplate 230 (see FIG. 2). Moreover, because matrix member 254 separates core member 252 and second endplate 230, there are no frictional or other contact forces generated between these two components as they move relative to one another. This may reduce the likelihood of mechanical failure. As described in further detail below, matrix member 254 may also provide a cushion that prevents the opposing endplates from coming into contact with one another during flexion or extension. This eliminates contact forces between the endplates and allows for the use of a wider range of non-metallic materials for the endplates. Additionally, by using a flexible and/or compressible matrix member, the present embodiments facilitate vertical cushioning during compression. That is, the vertical displacement between the upper and lower endplates at one end may be decreased, in part, by the vertical compression of the matrix member. This facilitates compression of the spine along the anterior side during flexion while also providing shock absorption.

In different embodiments, a variety of suitable materials could be used for the components of an ADR device. Suitable materials for a core member include, but are not limited to: metallic materials, plastic materials, and/or ceramic materials. Suitable materials for a matrix member include, but are not limited to: plastics and gels. Suitable materials for endplates include, but are not limited to: metallic materials, plastics, and/or ceramics. In one exemplary embodiment, a core member could be comprised of a polyether ether ketone (PEEK) material. Also, in one embodiment, a matrix member could be comprised of a suitably flexible gel. Additionally, in one embodiment, one or both endplates could be comprised of a suitable ceramic material.

The embodiments provide an artificial disc replacement that facilitates natural motion between vertebra. This is accomplished, in part, by the geometry of the core member, which has a curvature that varies over different regions. In particular, the curvature may vary between the posterior and anterior sides of the core member. That is, the radius of curvature changes from the posterior end to the anterior end.

Figure 7:
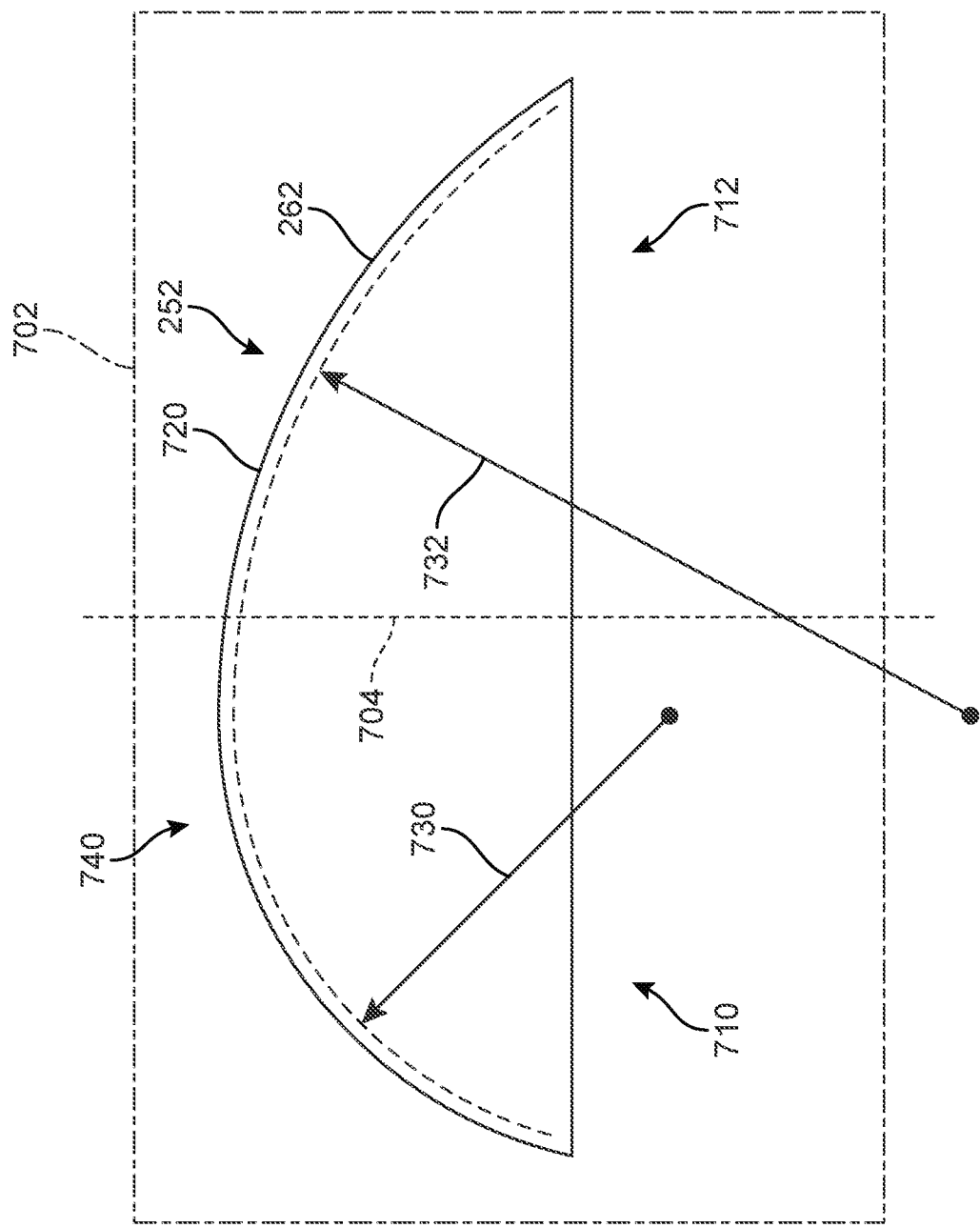
FIG. 7 is a side schematic view of a core member of an artificial disc replacement device in which the variable curvature of the upward engaging surface in the longitudinal direction is visible, according to an embodiment.

FIG. 7 is a schematic side view of core member 252. Visible within FIG. 7 is a sagittal plane 702 and a coronal plane 704 (shown here as a line). Coronal plane 704 divides core member 252 into a posterior side and an anterior side. Core member 252 further includes a posterior portion 710 associated with its posterior side and an anterior portion 712 associated with its anterior side.

The posterior and anterior portions may be associated with different degrees of curvature. In this description and in the claims, the curvature of a surface may be characterized by its radius of curvature, or arc radius. The arc radius of an arc, for example, is the radius of the circle of which the arc is a part. Moreover, the curvature of a local portion of a surface is inversely proportional to the associated arc radius of that local portion. In particular, a larger arc radius is associated with a smaller degree of curvature, while a smaller arc radius is associated with a larger degree of curvature.

As seen in FIG. 7, curved engaging surface 262 includes a curved boundary 720 that lies within sagittal plane 702. Curved boundary 720 has a curvature that varies along its length. Specifically, along posterior portion 710, curved boundary 720 has a first arc radius 730. Likewise, along anterior portion 712, curved boundary 720 has a second arc radius 732. As shown schematically in FIG. 7, first arc radius 730 is substantially smaller than second arc radius 732. This corresponds to a greater curvature for posterior portion 710 than for anterior portion 712.

In some embodiments, the arc radius of curved boundary 720 may gradually change between first arc radius 730 to second arc radius 732. This may occur within a transition portion 740 that is intermediate to posterior portion 710 and anterior portion 712. In some cases, the arc radius could vary smoothly from first arc radius 730 to second arc radius 732. In other cases, however, the arc radius could abruptly change.

In different embodiments, the relative sizes of each arc radius could vary. That is, their ratios could vary. In some embodiments, the ratio of the first arc radius to the second arc radius could vary in the range approximately between 1:2 and 9:10. In some embodiments, the ratio of the first arc radius to the second arc radius could be approximately 3:4. It may be appreciated that the ratio of the arc radii of the posterior and anterior ends may be suitably changed to accommodate different intended ranges of motion in different portions of the spine. For example, the ratio could have one value for implants used in the cervical spine and another ratio for implants used in the lumbar spine.

Additionally, the absolute sizes of each arc radius could vary in different embodiments. In some embodiments, the first arc radius could have a value approximately in the range between 4 and 6 centimeters. In one embodiment, the first arc radius could have a value of approximately 4.5 centimeters. In some embodiments, the second arc radius could have a value approximately in the range between 5 and 7 centimeters. In one embodiment, the first arc radius could have a value of approximately 6 centimeters. It may be appreciated that the absolute values of the arc radii of the posterior and anterior ends may be suitably changed to accommodate different intended ranges of motion in different portions of the spine. For example, the arc radii could have one set of value for implants used in the cervical spine and another set of values for implants used in the lumbar spine.

Figure 8:
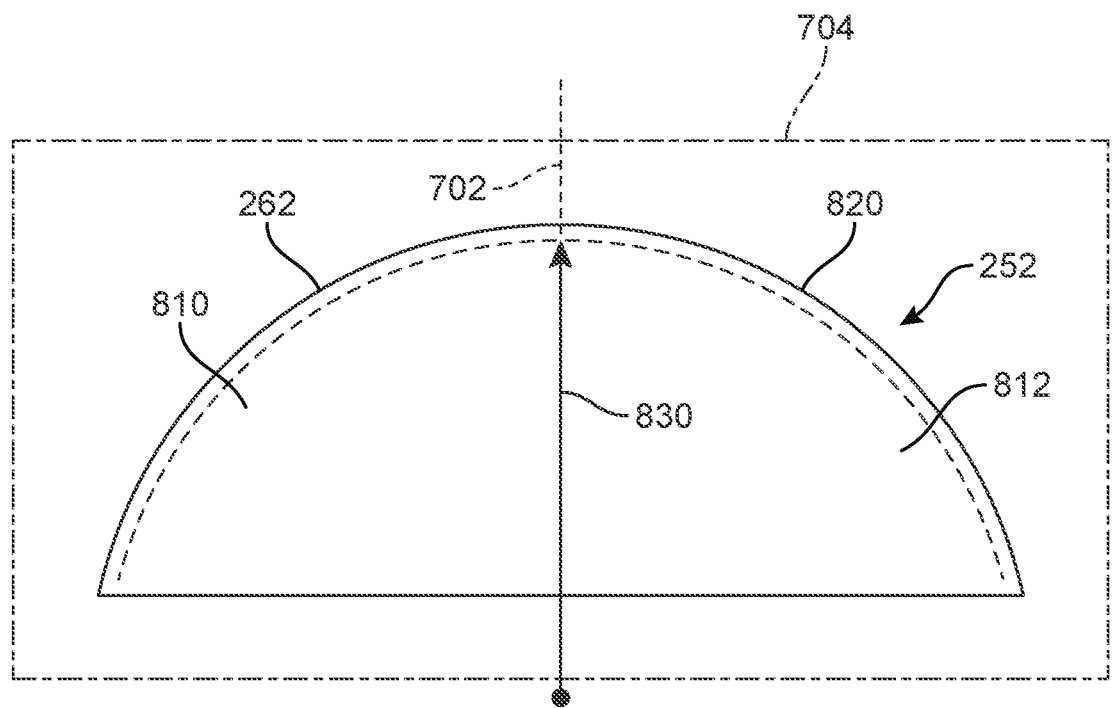
FIG. 8 is a schematic front view of the core member of FIG. 7 in which the constant curvature of the upward engaging surface in the lateral direction is visible.

FIG. 8 is a schematic cross-sectional front view of core member 252. Visible within FIG. 8 is sagittal plane 702 (shown here as a line) and coronal plane 704. Sagittal plane 702 divides core member 252 into opposing lateral sides. Core member 252 further includes a first lateral portion 810 associated with a first lateral side and a second lateral portion 812 associated with a second lateral side.

As seen in FIG. 8, curved engaging surface 262 includes a curved boundary 820 that lies within coronal plane 704. Curved boundary 820 has a substantially constant curvature. Specifically, curved boundary 820 has a substantially constant arc radius 830. This constant arc radius facilitates symmetric lateral bending on both sides of the body.

In some embodiments, arc radius 830 may be substantially smaller than first arc radius 730 and second arc radius 732 (see FIG. 7). In some embodiments, for example, the ratio of arc radius 830 to second arc radius 732 may be approximately 1:2. In some embodiments, arc radius 830 may have a value approximately in the range between 2 and 4 centimeters.

By using a core member with a curved engaging surface that has different arc radii in different regions, the implant described herein provides for natural motion between adjacent vertebra. In particular, the embodiments described herein allow the top endplate to tilt and slide forwards along the core member during forward flexion. Additionally, the embodiments help limit the tilting and rearward motion of the top endplate along the core member during rearward extension.

In embodiments where the width of a core member varies between the posterior and anterior ends, the arc radius of the outer boundary of the curved engaging surface could vary. However, in other embodiments, the arc radius of the outer boundary of the curved engaging surface could be substantially constant from the posterior end to the lateral end.

Figure 9:
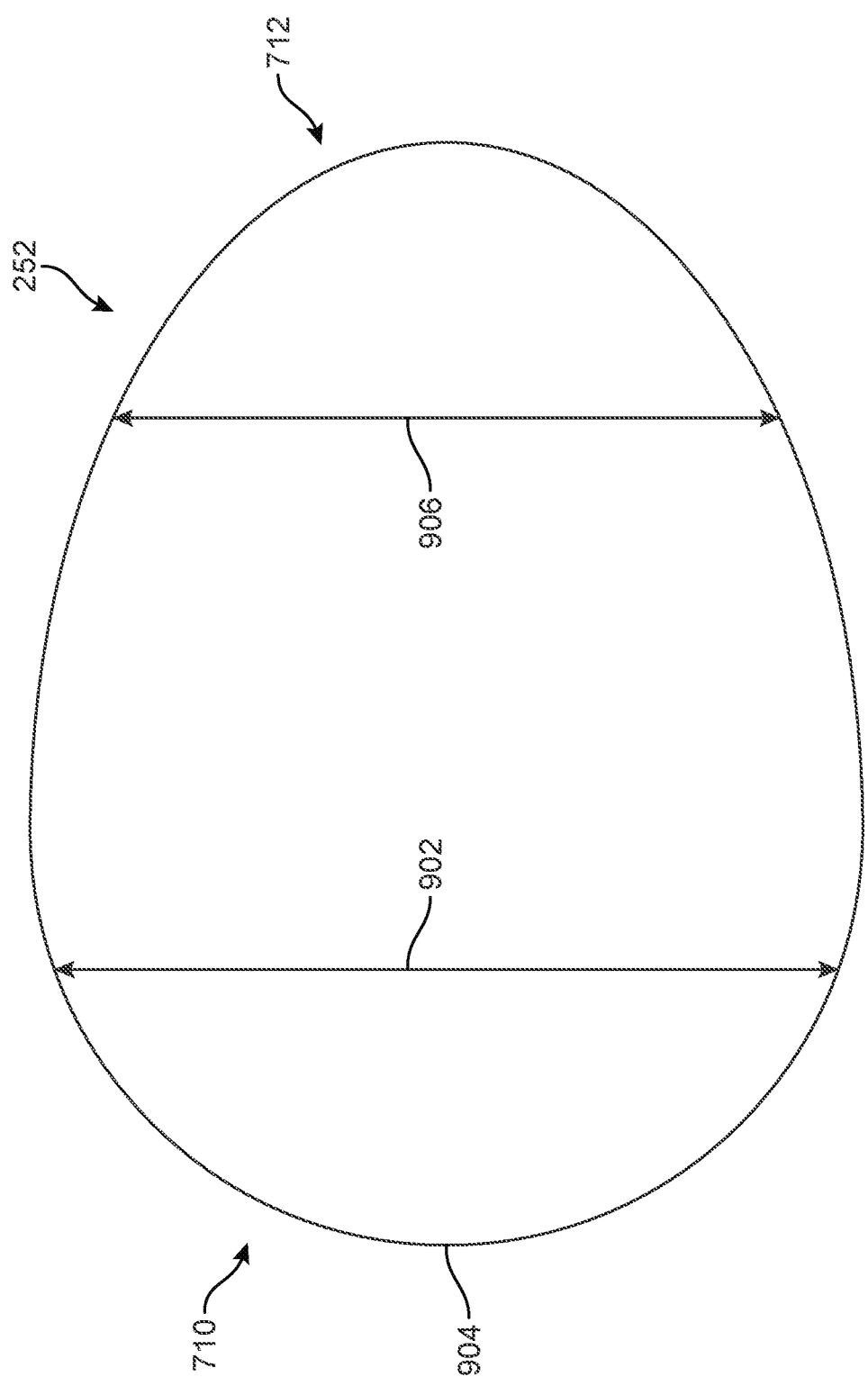
FIG. 9 is a schematic top-down view of an embodiment of a core member having a variable width.

FIG. 9 is a schematic top down view of core member 252 according to one embodiment. As seen in FIG. 9, the width of core member 252 may vary between posterior portion 710 and anterior portion 712. For example, posterior portion 710 may have a maximum width 902 that tapers quickly towards a posterior edge 904. Moreover, the width of core member 252 tapers from maximum width 902 in the direction of anterior portion 712. For reference, an intermediate width 906 is shown for a portion of anterior portion 712. Here, intermediate width 906 is substantially less than maximum width 902. This tapered geometry may help control bending in the lateral direction and allow for some twisting between core member 252 and first endplate 220 (see FIG. 2). In other embodiments, however, core member 252 could have an approximately constant width.

The present embodiments provide an ADR device that facilitates both translation and rotation of the upper endplate relative to the lower endplate without requiring the use of a core that can slide relative to either of the endplates. Instead, the curvature of the core member (including posterior and anterior ends with different arc radii) allow the center axis of rotation of the upper endplate to translate along the core member. This translation is depicted schematically in, for example, FIGS. 10-13 below.

Figure 10:
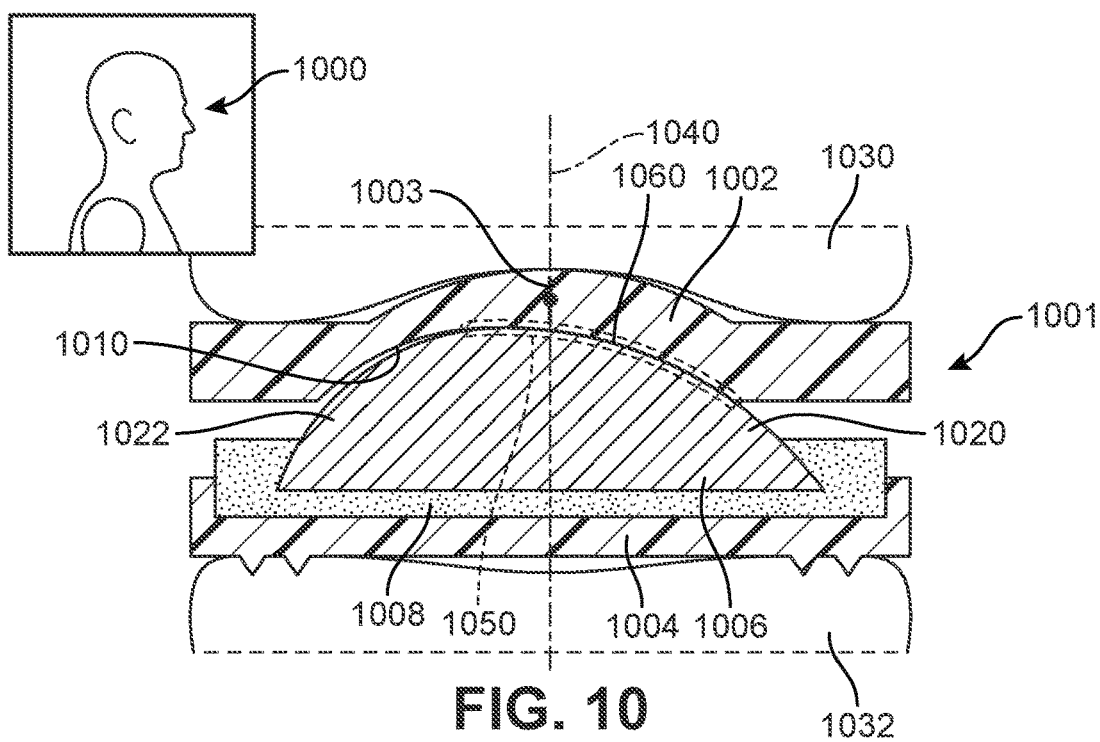
FIG. 10 is a schematic side view of a patient looking forward with an enlarged view of an artificial disc replacement device in a neutral position, according to an embodiment.

FIG. 10 is a schematic view of a patient 1000 who has a spinal implant. Adjacent to patient 1000 is an enlarged schematic view of spinal ADR device 1001 disposed between an upper vertebra 1030 and a lower vertebra 1032. Spinal ADR device 1001 further includes a first endplate 1002, a second endplate 1004, a core member 1006 and a matrix member 1008.

In FIG. 10, patient 1000 is standing in a neutral position. In this position, first endplate 1002 is disposed in neutral position with a central axis 1003 of first endplate 1002 aligned with a reference axis 1040. In this position, core member 1006 and recess 1010 of first endplate 1002 are in contact along a first contact area 1050. To facilitate motion of first endplate 1002 along the curved engaging surface 1060 of core member 1006, recess 1010 may be shaped to accommodate the smallest area of curvature on core member 1006. To accomplish this, the arc radius associated with recess 1010 may match that of the arc radius of the anterior portion 1020 of core member 1006. In the neutral position, therefore, the larger curvature of posterior portion 1022 may prevent contact between curved engaging surface 1060 and recess 1010 at posterior portion 1022.

Figure 11:
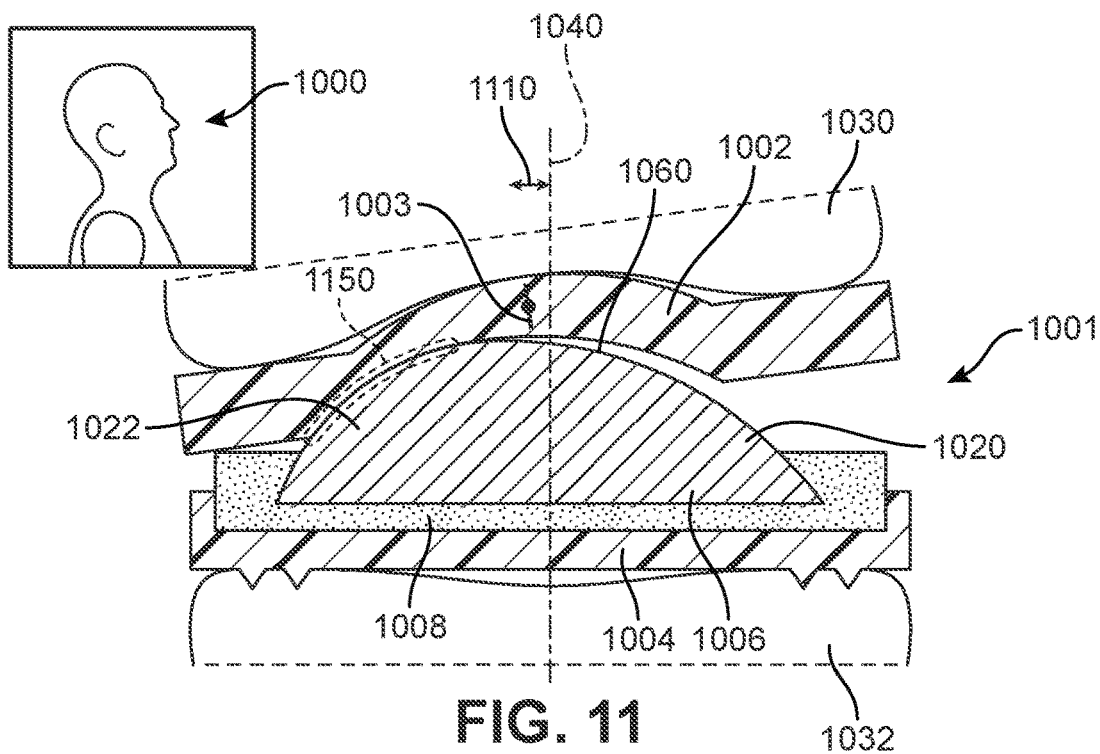
FIG. 11 is a schematic view of the patient of FIG. 10 in which their neck is undergoing extension with an enlarged view of a corresponding configuration of the artificial disc replacement device.

In FIG. 11, patient 1000 tilts his head backwards, causing adjacent vertebrae in the cervical spine to undergo extension. Referring to FIG. 11, as the cervical spine undergoes extension, first endplate 1002 is pushed backward and down the curved engaging surface 1060 until posterior portion 1022 of first endplate 1002 is engaged by matrix member 1008. In this position, core member 1006 and recess 1010 are in contact along a second contact area 1150.

Though matrix member 1008 may compress somewhat, depending on the amount of force applied by first end plate 1002, matrix member 1008 nonetheless acts to limit the rearward motion of first end plate 1002. Matrix member 1008 may also provide some cushioning and shock absorption following the initial contact between first end plate 1002 and matrix member 1008.

As seen in FIG. 11, during extension, first endplate 1002 may not only tilt but may be translated in the posterior direction. Here, central axis 1003 has been translated in the posterior direction by a distance 1110 and has also rotated with respect to reference axis 1040. However, the variable curvature of core member 1006 is configured to allow for substantially more translation in the anterior direction than in the posterior direction, as described in further detail below. The result is that there is significantly less compression between the endplates at posterior portion 1022 during extension as there is between the endplates at anterior portion 1020 during flexion. This has the effect of limiting the relative translation between vertebrae during extension and, accordingly, how much the cervical spine can extend back.

Figure 12:
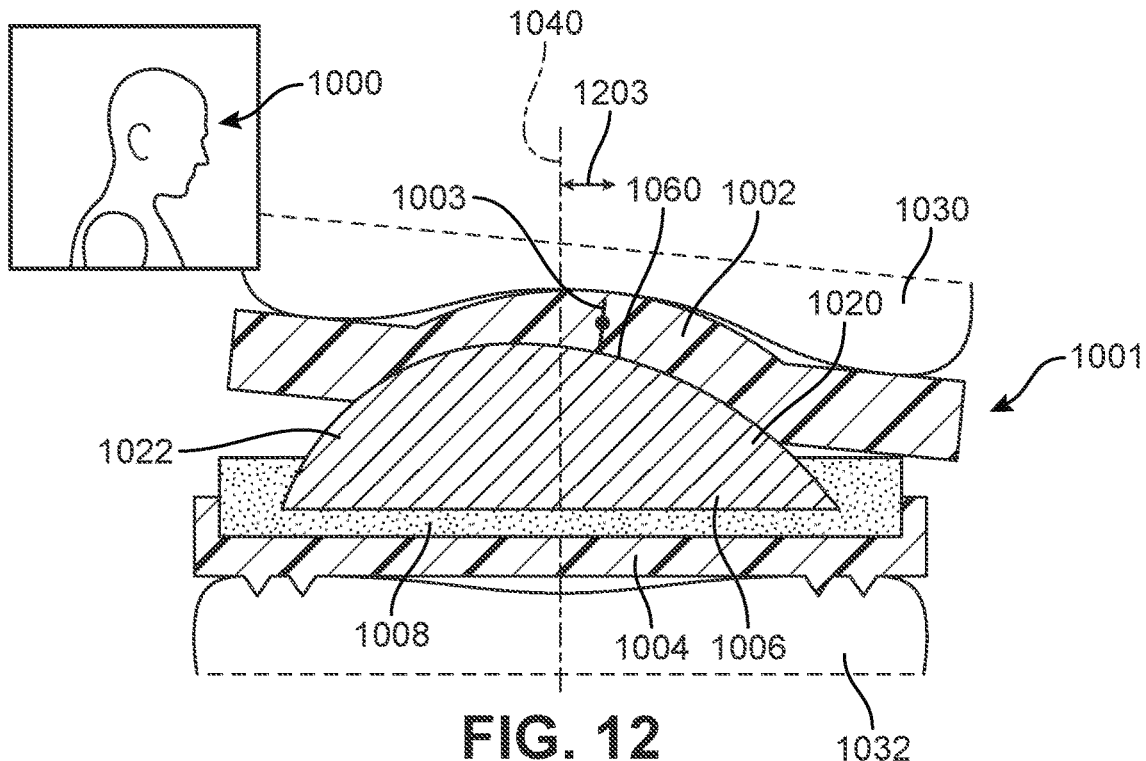
FIG. 12 is a schematic view of the patient of FIG. 10 in which their neck is undergoing flexion with an enlarged view of a corresponding configuration of the artificial disc replacement device.

In FIG. 12, patient 1000 bends his neck forward, causing adjacent vertebrae in the cervical spine to undergo flexion. Referring to FIG. 12, as the spine bends, first endplate 1002 is pushed forward and down the curved engaging surface 1060 until anterior portion 1020 first endplate 1002 is engaged by matrix member 1008.

In FIG. 12, as patient 1000 continues pressing his neck down until his chin touches his chest, first endplate 1002 may slide further down curved engaging surface 1060. Additionally, matrix member 1008 may be compressed, further accommodating the forward translation of first endplate 1002 and decreasing the relative distance between the top of first endplate 1002 and the bottom of second endplate 1004 along the anterior side. In this position, core member 1006 and recess 1010 are in contact along a third contact area 1350. Because recess 1010 is sized to fit the larger arc radius of anterior portion 1020, third contact area 1350 may be substantially larger than, for example, the contact area 1050 when the device is in a neutral position (see FIG. 10).

Figure 13:
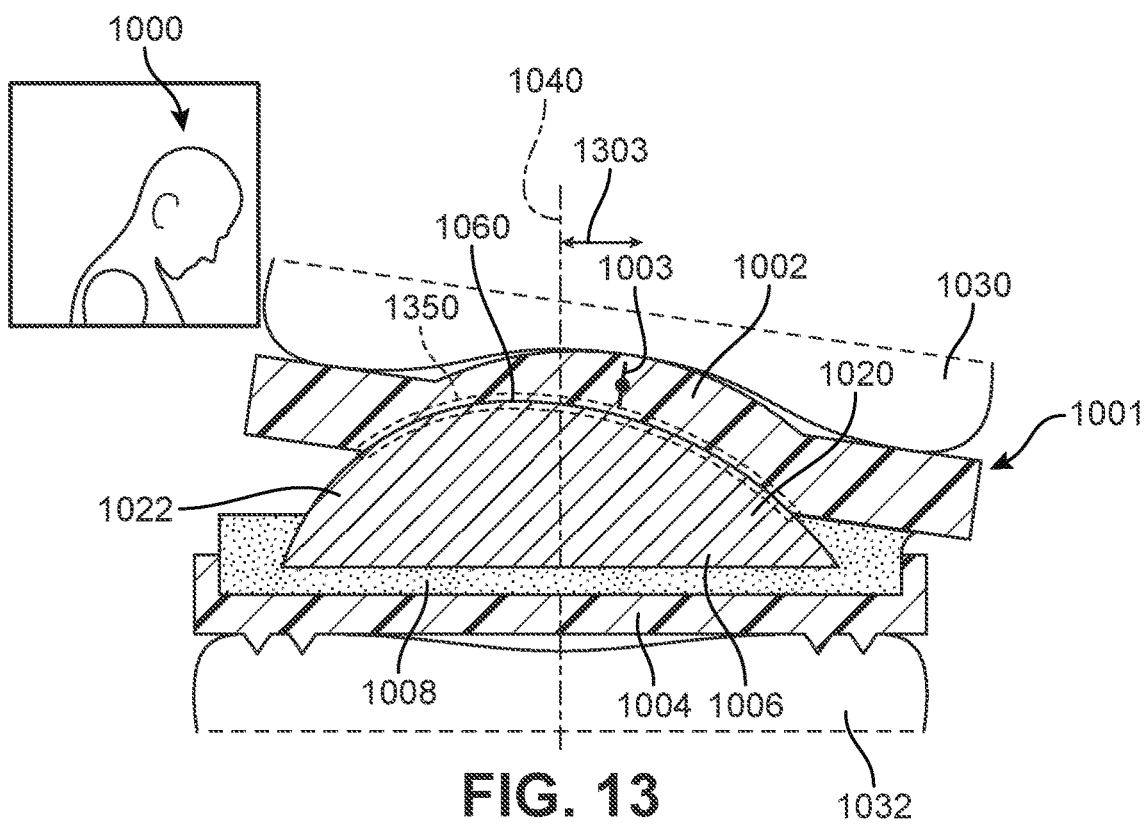
FIG. 13 is a schematic view of the patient of FIG. 10 in which their neck is undergoing further flexion with an enlarged view of a corresponding configuration of the artificial disc replacement device.

As seen in FIGS. 12-13, during flexion, first endplate 1002 may not only tilt but may be translated in the anterior direction. This can be seen clearly by comparing the position of central axis 1003 with reference axis 1040 (which represents the initial position of central axis 1003 in the neutral position). Here, central axis 1003 has been translated in the anterior direction by a distance 1203 (in FIG. 12) and by a distance 1303 (in FIG. 13). Additionally, in both FIGS. 12 and 13, central axis 1003 has also rotated with respect to reference axis 1040. In this exemplary configuration, first endplate 1002 may be configured to translate by as much as 1 to 3 millimeters in the anterior direction. This allows the adjacent vertebrae to move as they normally would under flexion.

Using a configuration in which the upper endplate can not only tilt but also translate in the anterior direction relative to the lower endplate allows the adjacent vertebrae to achieve the necessary degree of compression so that a patient's neck can move through the entire range of normal motion, including putting his chin against his chest. Moreover, using a relatively less rigid matrix member provides shock absorption during flexion and prevents the upper endplate from coming into contact with the lower endplate. Thus, the present ADR device acts to provide an increased range of motion in the neck during flexion and a more limited range of motion in the next during extension, accommodating the natural motions of the neck.

Figure 14:
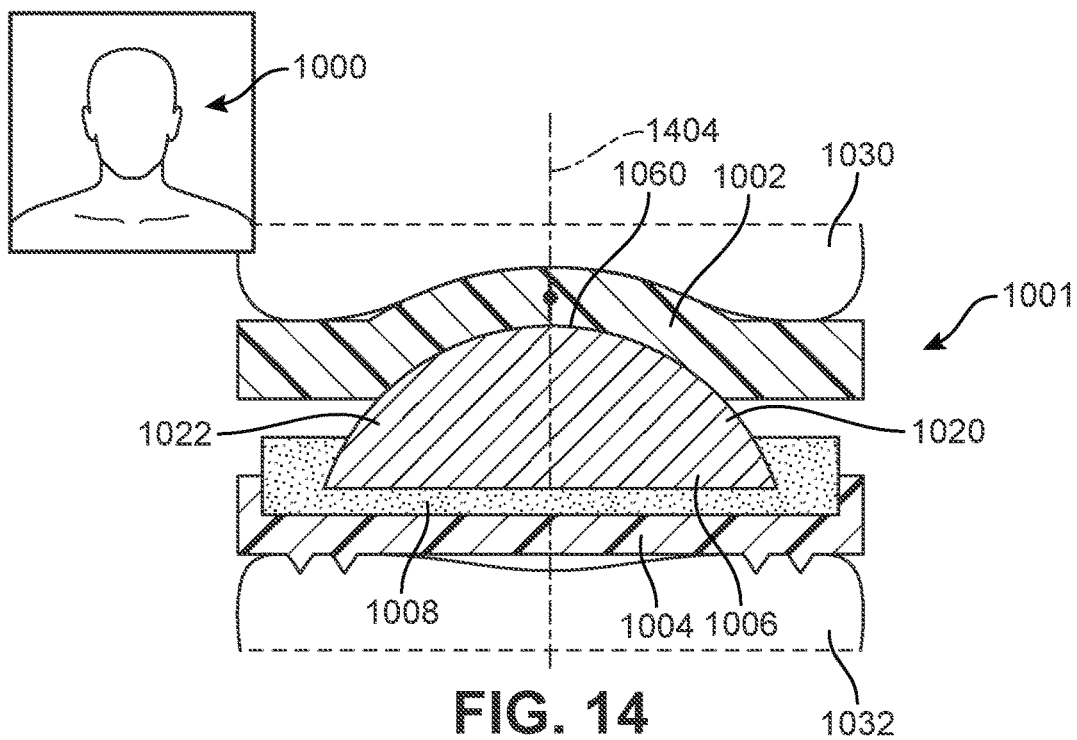
FIG. 14 is a schematic front view of a patient looking forward with an enlarged view of an artificial disc replacement device in a neutral position, according to an embodiment.
Figure 15:
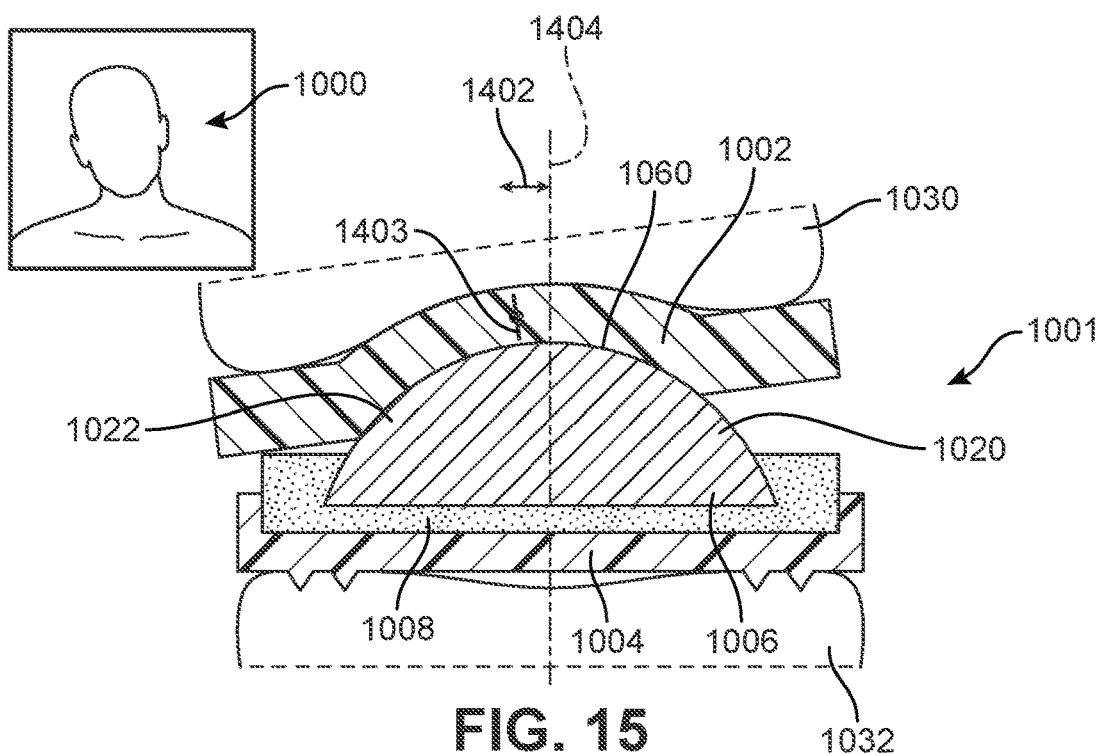
FIG. 15 is a schematic view of the patient of FIG. 14 in which their neck is undergoing lateral bending with an enlarged view of a corresponding configuration of the artificial disc replacement device.

FIG. 14 is a schematic front view of patient 1000 in a neutral position with an enlarged view of device 1001. As seen in FIG. 15, as patient 1000 bends his neck laterally, first endplate 1002 travels down curved engaging surface 1060. During this motion, a central axis 1403 of first endplate 1002 travels laterally by a distance 1402 compared to a reference axis 1404. Because curved engaging surface 1060 has a smaller arc radius along its lateral sides than along its posterior or anterior sides, the degree of motion is more limited than during extension or flexion. Moreover, because curved engaging surface 1060 has a substantially constant arc radius, the degree of bending is equal on both sides.

As already described above, the embodiments not only control the motion of the upper endplate so as to mimic the natural motion of two adjacent vertebrae, but the presence of the softer matrix member substantially eliminates contact between the upper and lower endplates. Typically, endplates must be constructed from high strength materials such as metals that can withstand large contact forces as the endplates collide during flexion and/or extension. Since the current design eliminates contact between the endplates, the endplates can be manufactured from non-metallic materials. For example, in some embodiments, the endplates could be manufactured from plastic materials and/or ceramic materials that provide better biocompatibility with vertebra, improved wear characteristics and different degrees of strength compared to metal materials. Moreover, the use of non-metallic materials in the ADR device may substantially reduce or eliminate the metallic artifacts that may arise in MRIs when metallic prosthetics are present in the spine.

Figure 16:
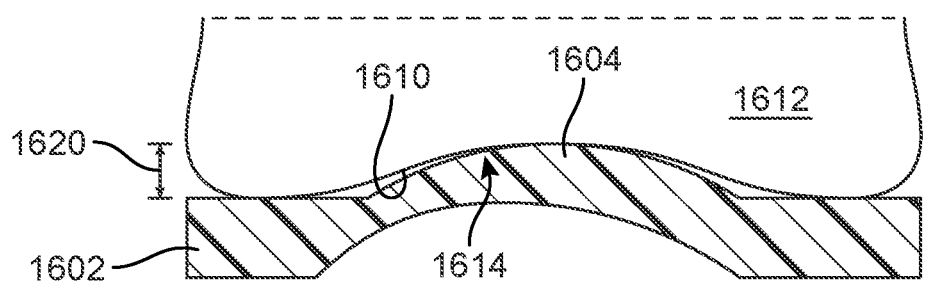
FIG. 16 is a schematic view of an endplate of an artificial disc replacement device with a centrally located dome for engaging a recess in an adjacent vertebra, according to an embodiment.
Figure 17:
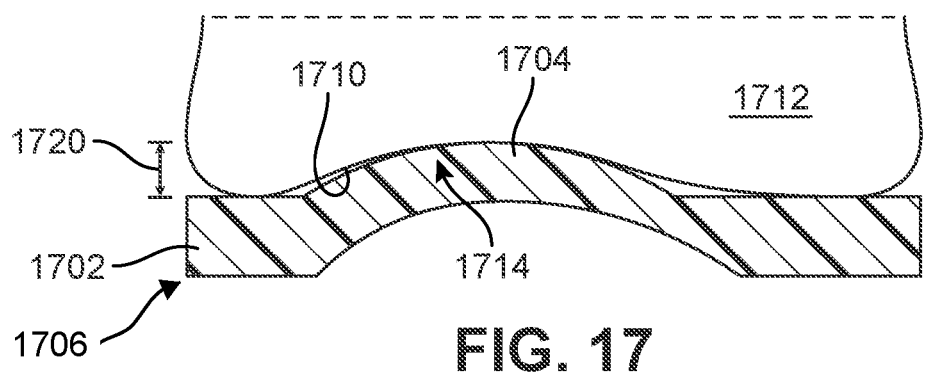
FIG. 17 is a schematic view of an endplate of an artificial disc replacement device with a posteriorly located dome for engaging a recess in an adjacent vertebra, according to an embodiment.
Figure 18:
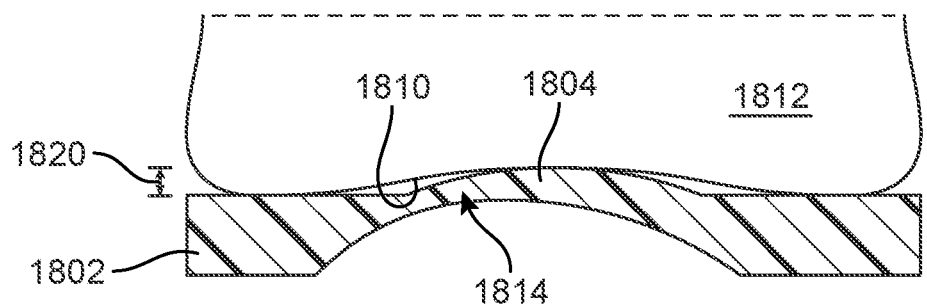
FIG. 18 is a schematic view of an endplate of an artificial disc replacement device with a relatively flat dome for engaging a corresponding flat recess in an adjacent vertebra, according to an embodiment.

In different embodiments, the size and/or relative position of a dome on an upper endplate can vary. For example, FIGS. 16-18 depict three different embodiments in which the dome on the upper endplate varies in size and/or position. Different dome shapes and/or positions can be selected during surgery to facilitate better connection with the upper vertebra. Specifically, the dome may be better aligned and may fit better with the natural shape of the inferior side of the vertebra.

In FIG. 16, upper endplate 1602 is configured with a dome 1604 that is substantially centered along the endplate. Such a configuration may be most useful for engaging the inferior side 1610 of a vertebra 1612 with a centrally located concave region 1614. In FIG. 17, upper endplate 1702 is configured with a dome 1704 that is disposed closer to posterior end 1706 of upper endplate 1702. Such a configuration may be most useful for engaging the inferior side 1710 of a vertebra 1712 with a posteriorly located concave region 1714. In FIG. 18, upper endplate 1802 is configured with a substantially flatter dome 1804 compared to dome 1604 and dome 1704. For example, dome 1804 may have a height 1820 compared to a substantially larger height 1620 for dome 1604 and height 1720 for dome 1704. Such a configuration may be most useful for engaging the inferior side 1810 of a vertebra 1812 with a relatively shallow concave area 1814.

Embodiments can include additional provisions to prevent contact between opposing endplates in an ADR device. In some embodiments, a matrix member can be shaped to extend radially outward over the lower endplate so that no portion of the lower endplate is exposed on a superior side.

Figure 19:
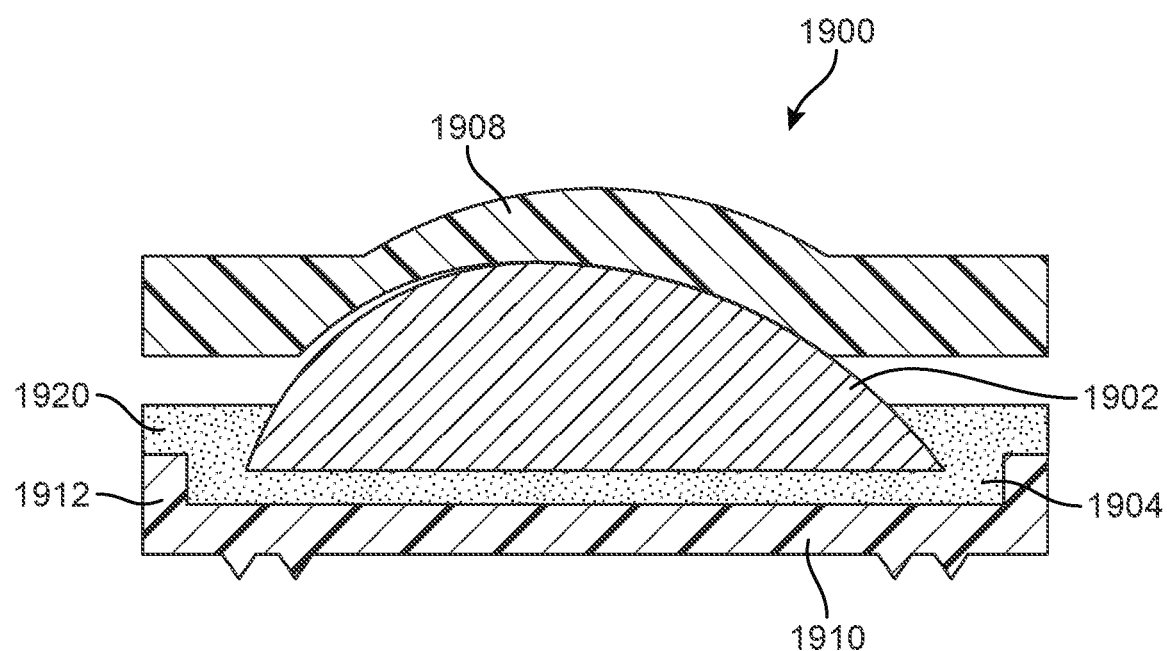
FIG. 19 is a schematic view of another embodiment of a core assembly and a lower endplate, in which a matrix member of the core assembly covers an entirety of the lower endplate.

FIG. 19 depicts an alternative embodiment of part of an ADR device 1900 that includes a core member 1902, a matrix member 1904, an upper endplate 1908 and a lower endplate 1910. As seen in FIG. 19, matrix member 1904 includes a peripheral portion 1920 that extends over a peripheral lip 1912 of lower endplate 1910. Using this configuration, matrix member 1904 completely covers the superior side of lower endplate 1910 and prevents any contact between lower endplate 1910 and upper endplate 1908.

The exemplary ADR device can be implanted into a patient's spine using a suitable surgical method. In some embodiments, after removing some or all of the tissue between adjacent vertebrae, a surgeon may first implant the upper and lower endplates. For example, the surgeon may place the lower endplate against one vertebra. In cases where the lower endplate includes teeth or similar provisions, the surgeon may apply pressure and/or tap the endplate to that the teeth engage the vertebra and prevent the lower endplate from moving with respect to the vertebra. The upper endplate may also be placed against the opposing vertebra. Specifically, an upper endplate with a suitable dome for engaging a concave area in the vertebra can be selected. As described above, a surgeon could choose from at least endplates with domes that are either centrally or posteriorly located. Also, a surgeon could choose from at least endplates with domes that have different overall heights. Once a suitable endplate has been selected, the endplate can be inserted and placed against the vertebra so that the dome engages the concave area of vertebra.

Once the endplates have been positioned and/or fixed in place, a surgeon may insert a core assembly comprising both a core member and a matrix member. To insert the core assembly, the surgeon can insert the matrix member into a corresponding recess of the lower endplate while simultaneously inserting a portion of the core member into a corresponding recess of the upper endplate. Once the core member has been inserted, the compressive forces of the spine may act to keep the matrix member fixed in the recess of the lower endplate and the core member engaged with the recess of the upper endplate.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with, or substituted for, any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An artificial disc replacement device, comprising:
a first endplate configured to be disposed against a first vertebrae in a spine and a second endplate configured to be disposed against a second vertebrae in the spine;
a core member disposed between the first endplate and the second endplate, the core member having a curved engaging surface for engaging the first endplate;
the core member including a sagittal plane that separates the core member into a first lateral side and a second lateral side;
the core member also including a coronal plane that separates the core member into an anterior side and a posterior side;
wherein the curved engaging surface includes a curved boundary that extends within a first plane that is parallel with the sagittal plane;
wherein the curved boundary has a first arc radius along an anterior portion disposed on the anterior side of the core member;
wherein the curved boundary has a second arc radius along a posterior portion disposed on the posterior side of the core member, wherein the second arc radius is substantially different from the first arc radius;
wherein the curved boundary of the curved engaging surface has a substantially constant curvature in a second plane that is parallel with the coronal plane;
wherein the device is configured to articulate between the core member and the first endplate; and
wherein the core member and the second endplate are configured to remain substantially fixed with respect to one another.

2. The artificial disc replacement device according to claim 1, wherein the artificial disc replacement device further includes a matrix member disposed between the core member and the second endplate.

3. The artificial disc replacement device according to claim 2, wherein the matrix member is substantially more compressible than the core member.

4. The artificial disc replacement device according to claim 2, wherein the matrix member substantially covers a superior side of the second endplate to prevent the first endplate from contacting the second endplate.

5. The artificial disc replacement device according to claim 1, wherein the first arc radius is larger than the second arc radius.

6. The artificial disc replacement device according to claim 1, wherein in a neutral position of the artificial disc replacement device, the posterior portion is prevented from contacting a recess of the first endplate; and
wherein during extension at least some of the posterior portion contacts the recess.

7. The artificial disc replacement device according to claim 1, wherein the first endplate has a central axis;
wherein, as the artificial replacement device undergoes flexion, the central axis of the first endplate is translated in an anterior direction;
wherein as the artificial replacement device undergoes extension the central axis of the first endplate is translated in a posterior direction; and
wherein the geometry of the interface between the curved engaging surface and a recess of the first endplate enables the central axis of the first endplate to translate further in the anterior direction during flexion than in the posterior direction during extension.

8. The artificial disc replacement device according to claim 1, wherein the first endplate has a recess that accommodates the curved engaging surface of the core member; and
wherein at least a portion of the recess has an arc radius within the sagittal plane that is substantially similar to the first arc radius of the core member to enable forward translation and tilting of the first endplate relative to the second endplate during flexion.

9. An artificial disc replacement device, comprising:
a first endplate configured to be disposed against a first vertebrae in a spine and a second endplate configured to be disposed against a second vertebrae in the spine;
a core member disposed between the first endplate and the second endplate, the core member having a curved engaging surface for engaging the first endplate;
wherein the curved engaging surface includes a curved boundary that extends within a first plane;
wherein the curved boundary has a first arc radius along an anterior portion of the core member;
wherein the curved boundary has a second arc radius along a posterior portion of the core member, wherein the second arc radius is substantially different from the first arc radius;
wherein the curved boundary of the curved engaging surface has a substantially constant curvature in a second plane that is substantially perpendicular to the first plane;
wherein the device is configured to articulate between the core member and the first endplate; and
wherein the core member and the second endplate are configured to remain substantially fixed with respect to one another.

10. The artificial disc replacement device according to claim 9, wherein the first endplate has a recess with a geometry that accommodates the curved engaging surface of the core member.

11. The artificial disc replacement device according to claim 10, wherein at least a portion of the recess has an arc radius within the first plane that is substantially similar to the first arc radius of the core member to enable forward translation and tilting of the first endplate relative to the second endplate during flexion.

12. The artificial disc replacement device according to claim 9, wherein the artificial disc replacement device further includes a matrix member disposed between the core member and the second endplate.

13. The artificial disc replacement device according to claim 12, wherein the matrix member is substantially more compressible than the core member.

14. The artificial disc replacement device according to claim 12, wherein the matrix member substantially covers a superior side of the second endplate to prevent the first endplate from contacting the second endplate.

* * * * *